United States Patent
Malhotra et al.

(10) Patent No.: US 12,384,784 B2
(45) Date of Patent: Aug. 12, 2025

(54) POLYMORPHS OF ACALABRUTINIB, A BRUTON'S TYROSINE KINASE INHIBITOR

(71) Applicant: CIPLA LIMITED, Maharashtra (IN)

(72) Inventors: Geena Malhotra, Mumbai (IN); Venkata Srinivas Pullela, Bangalore (IN); Srinivas Laxminarayan Pathi, Bangalore (IN); Ramanaiah Chennuru, Andhra Pradesh (IN); Ramesh Devarapalli, Andhra Pradesh (IN); Ashok Mithun, Bangalore (IN)

(73) Assignee: Cipla Limited, Maharashtra (IN)

( * ) Notice: Subject to any disclaimer, the term of this patent is extended or adjusted under 35 U.S.C. 154(b) by 1056 days.

(21) Appl. No.: 17/279,235

(22) PCT Filed: Sep. 24, 2019

(86) PCT No.: PCT/IN2019/050696
§ 371 (c)(1),
(2) Date: Mar. 24, 2021

(87) PCT Pub. No.: WO2020/065667
PCT Pub. Date: Apr. 2, 2020

(65) Prior Publication Data
US 2022/0002302 A1    Jan. 6, 2022

(30) Foreign Application Priority Data
Sep. 25, 2018    (IN) .............................. 201821036102

(51) Int. Cl.
*C07D 487/04*    (2006.01)
(52) U.S. Cl.
CPC ........ *C07D 487/04* (2013.01); *C07B 2200/13* (2013.01)
(58) Field of Classification Search
CPC .... C07D 487/04; C07B 2200/13; A61P 35/00
See application file for complete search history.

(56) References Cited

FOREIGN PATENT DOCUMENTS

WO    2017002095 A1    1/2017

OTHER PUBLICATIONS

International Search Report and Written Opinion issued in PCT/IN2019/050696, dated Dec. 16, 2019, 15 pages.

*Primary Examiner* — Joseph K McKane
*Assistant Examiner* — David M Shim
(74) *Attorney, Agent, or Firm* — Meunier Carlin & Curfman LLC

(57) ABSTRACT

The present invention discloses novel crystalline polymorphic forms of Acalabrutinib, methods of preparation, pharmaceutical compositions and methods of therapeutic treatment involving polymorphic forms thereof.

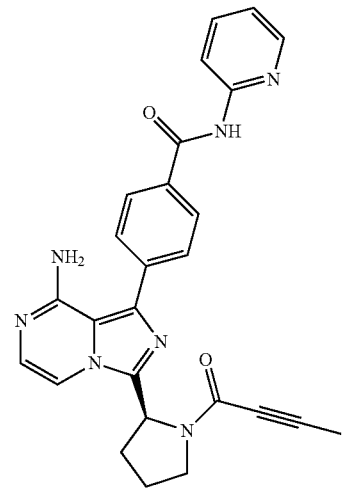

6 Claims, 6 Drawing Sheets

POLYMORPHS OF ACALABRUTINIB, A BRUTON'S TYROSINE KINASE INHIBITOR

TECHNICAL FIELD OF THE INVENTION

The present invention relates to new polymorphs of Bruton's tyrosine kinase inhibitor, processes for the preparation of the new polymorphs, pharmaceutical compositions containing these new polymorphs and use of such composition in treatment of cancer.

BACKGROUND

Acalabrutinib is a second generation Bruton's tyrosine kinase inhibitor developed by Acerta Pharma. Chemically Acalabrutinib is known as 4-{8-amino-3-[(2S)-1-(but-2-ynoyl)pyrrolidin-2-yl]imidazo[1,5-a]pyrazin-1-yl)}-N-(pyridine-2-yl)benzamide. The structure of Acalabrutinib is represented as follows:

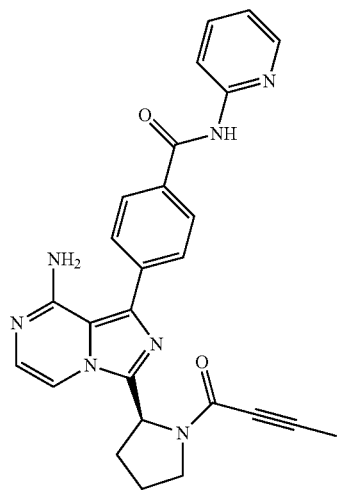 [SMILES: CC#CC(=O)N1CCC[C@H]1c1nc(-c2ccc(C(=O)Nc3ccccn3)cc2)c2c(N)nccn12]

Acalabrutinib is indicated for the treatment of adult patients with mantle cell lymphoma (MCL).

Acalabrutinib and its preparation was first disclosed in WO2013010868 along with other compounds. WO2017002095 describes various polymorphs of Acalabrutinib such Form I, II, III, IV, V, VI, VII, VIII, amorphous form, Form A of citrate salt, Form A of gentisate salt, Form A of oxalate salt, Form A of sulphate salt, Form A of maleate salt, Form A of fumarate salt, phosphate salt, L-tartrate, Cocrystals—with L-arabitol, L-proline, D-sorbitol, succinic acid and amorphous dispersions with various polymers.

WO2018064797 which is in Chinese language describes form 1, form 2 and form 3 as appeared from Google translation. While WO2018148961 which is also in Chinese language, describes Form 1 & amorphous form of malate salt, Form 1 of hemi-fumarate salt, Form 1 of maleate salt, Form 1 of phosphate salt, Form 1 of sulphate salt.

WO 2019159097 patent application publication describes form S and form S2 of Acalabrutinib which are characterized by XRD, DSC, IR and TGA.

It is a well known fact that different polymorphic forms of the same drug may have substantial differences in certain pharmaceutically important properties such as dissolution characteristics, bioavailability patterns, handling properties, solubility, flow characteristics and stability.

Further, different physical forms may have different particle size, hardness and glass transition temperatures.

The discovery of new polymorphic forms of a pharmaceutically useful compound provides a new opportunity to improve the performance characteristics of a pharmaceutical product.

These polymorphic forms exhibit distinct X-ray diffractogram, solid state $^{13}$C NMR spectrometry, infrared spectrometry. Further, these polymorphic forms may give rise to peculiar thermal behaviour which can be measured by melting point, thermogravimetric analysis (TGA), differential scanning calorimetry (DSC). All these properties can be used to distinguish a particular polymorph from the other form.

OBJECTIVES OF THE INVENTION

The object of the invention is to provide new polymorphic forms of Acalabrutinib and processes for the preparation of these new polymorphic forms of Acalabrutinib.

Another object of the present invention is to provide pharmaceutical compositions comprising new polymorphic forms of Acalabrutinib.

Yet another aspect of the present invention is to provide pharmaceutical compositions comprising new polymorphic forms of Acalabrutinib for use in medical treatment of cancer.

SUMMARY OF THE INVENTION

In one aspect, the invention provides new polymorphic forms which hereinafter are referred to as crystalline form (also known as "polymorph") Form-C2, Form-C3, Form-C4 and Form-C5 of Acalabrutinib.

In another aspect, the invention provides processes for the preparation of new polymorphic forms of Acalabrutinib.

In yet another aspect, the invention provides pharmaceutical compositions comprising new polymorphic forms of Acalabrutinib along with a pharmaceutically acceptable carrier.

In further aspect, the invention provides use of the pharmaceutical compositions comprising new polymorphic forms of Acalabrutinib along with a pharmaceutically acceptable carrier in treatment of cancer.

DETAILED DESCRIPTION OF THE INVENTION

Figure 1:
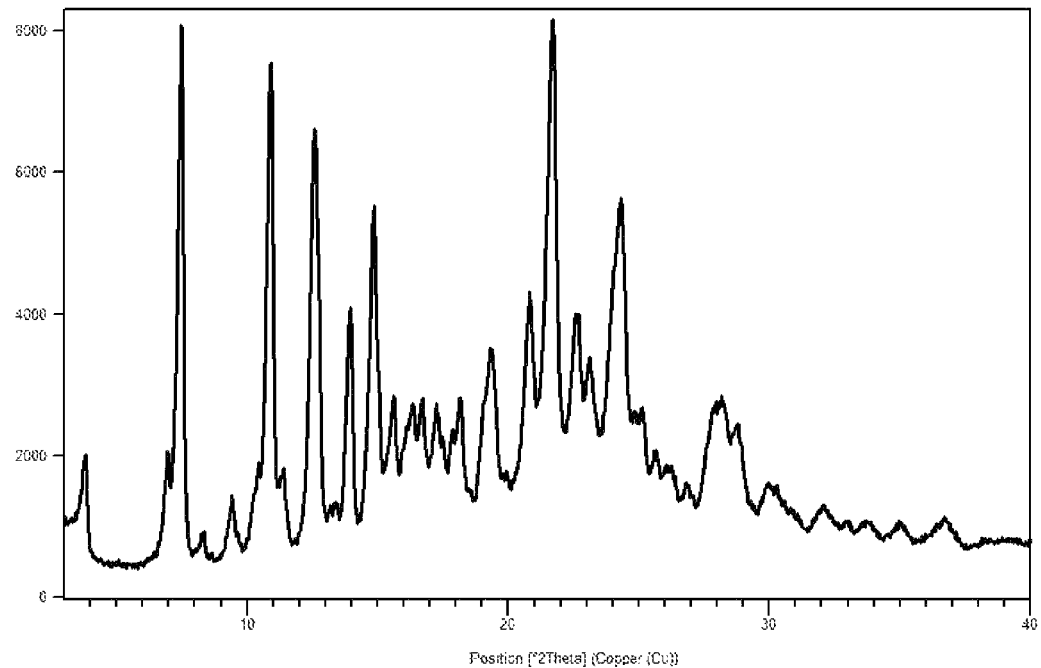
FIG. 1 represents a powder X-ray diffraction pattern of Form-C2 of Acalabrutinib.

The invention will now be described in its various preferred as well as optional embodiments, so that the various aspects therein will be more clearly understood and appreciated.

The present invention relates to crystalline Acalabrutinib polymorphs, the process for preparation thereof and pharmaceutical compositions containing said polymorphs as active ingredient.

As used herein, the term "PXRD" refers to powder X-ray diffraction, the term "IR" refers to infrared, the term "NMR" refers to nuclear magnetic resonance, the term "TGA" refers to thermogravimetric analysis, the term "DSC" refers to differential scanning calorimetry and the term "DVS" refers to dynamic vapour sorption isotherm.

As used herein, the term "substantially the same X-ray powder diffraction pattern" is understood to mean that those X-ray powder diffraction patterns having diffraction peaks with 2θ values within ±0.2° of the diffraction patterns referred to herein are within the scope of the referred to diffraction pattern.

As used herein, the term "solvate" refers to an association or complex of one or more solvent molecules and a compound of the invention. Such solvents for the invention may not interfere with the biological activity of the solute. Typically, the solvent used is a pharmaceutically acceptable solvent.

The solvate can be isolated either as an amorphous form or in a crystalline form, preferably in crystalline form.

The solvate can be further isolated either in anhydrous form or hydrated form.

As used herein, the term "hydrate" refers to the complex where the solvent molecule is water. The skilled person will appreciate that the water molecules are absorbed, adsorbed or contained within a crystal lattice of the solid compounds, usually in defined stoichiometric ratio. The notation for a hydrated compound may be. $nH_2O$, where n is the number of water molecules per formula unit of the compound. For example, in a hemihydrate, n is 0.5; in a monohydrate n is one; in a sesquihydrate, n is 1.5; in a dihydrate, n is 2; and so on.

The novel polymorphs of the present invention may be isolated in pseudo polymorphic form as a solvate optionally in hydrated form, or as a non-hydrated solvate.

As polymorphic forms are reliably characterized by peak positions in the X-ray diffractogram, the polymorphs of the present invention have been characterized by powder X-ray diffraction spectroscopy which produces a fingerprint of the crystalline form and is able to distinguish it from all other crystalline and amorphous forms of Acalabrutinib. Measurements of 2θ values are accurate to within ±0.2 degrees. All the powder diffraction patterns were measured on a PANalytical X'Pert[3] X-ray powder diffractometer with a copper-K-α radiation source.

The invention will now be described in detail in connection with certain preferred and optional embodiments, so that various aspects thereof may be more fully understood and appreciated.

Thus, in one aspect, the present invention provides the crystalline Acalabrutinib which is herein and in the claims designated as "Form-C2".

In one embodiment, the crystalline Form-C2 is characterized by an X-ray powder diffraction pattern comprising the following 2θ values measured using CuKα, radiation.

In an embodiment, the crystalline Form-C2 has an XRD pattern with characteristics peaks at 7.4, 10.9, 12.5, 13.9, 14.8, 20.8, 21.6 and 22.6±0.2° 2θ.

Crystalline Form-C2 of Acalabrutinib may be characterized by powder X-ray diffraction pattern, as shown in FIG. 1.

Crystalline Form-C2 may further also contain water in it. The water content may be in the range of 1 to 2%.

Those skilled in the art would recognize that Form-C2 may be further characterized by other methods including, but not limited to IR, solid state NMR, DSC, TGA, intrinsic dissolution and Raman spectroscopy.

In another embodiment, the invention provides process for preparation of crystalline Form-C2 of Acalabrutinib which process involves mixing Acalabrutinib with toluene solvent. This process of mixing is carried out at 20° C. to 30° C. The reaction mixture was then stirred at higher temperature at about 60° C. to 100° C. for 1 to 2 hours. The so obtained reaction mass was then cooled to 20° C. to 30° C. and filtered under vacuum. The resultant solid material was dried to get crystalline Form-C2.

According to second aspect, the present invention provides the crystalline Acalabrutinib which is herein and in the claims designated as "Form-C3".

In one embodiment, the crystalline Form-C3 is characterized by an X-ray powder diffraction pattern comprising the following 2θ values measured using CuKα, radiation.

In an embodiment, the crystalline Form-C3 has an XRD pattern with characteristics peaks at 8.5, 10.0, 11.7, 12.9, 15.3, 17.9, 18.3, 20.1 and 21.6±0.2° 2θ

Figure 2:
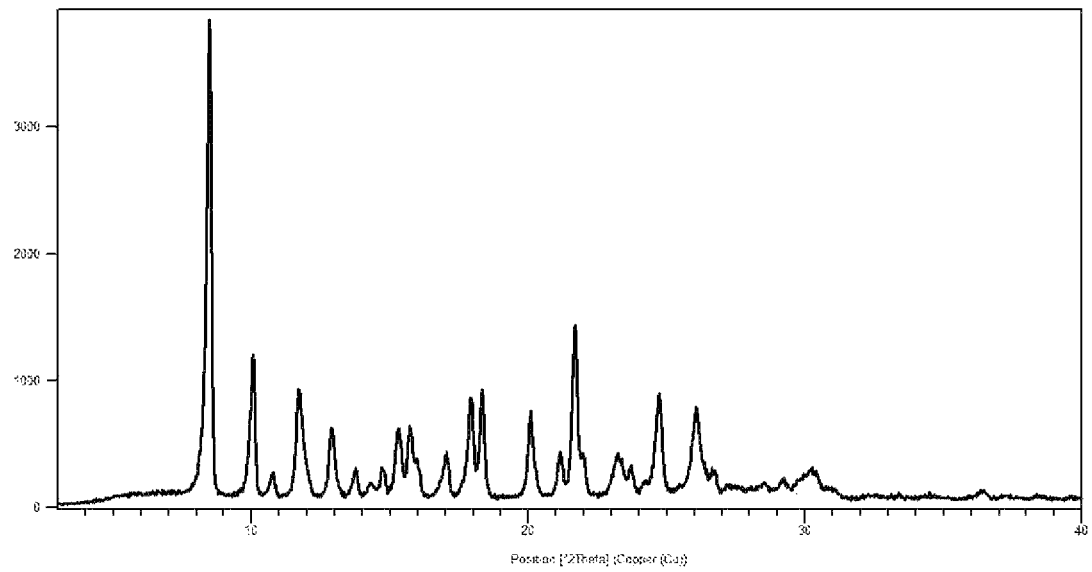
FIG. 2 represents a powder X-ray diffraction pattern of Form-C3 of Acalabrutinib.

Crystalline Form-C3 of Acalabrutinib may be characterized by powder X-ray diffraction pattern, as shown in FIG. 2.

Crystalline Form-C3 of Acalabrutinib may also be characterized as having a DSC spectrum. The DSC plot for the sample shows one endotherm with an onset at 95.65° C., a peak maximum at 113.70° C.; and a second endotherm with an onset at 141.49° C. and a peak maximum at 152.86° C.

Figure 3:
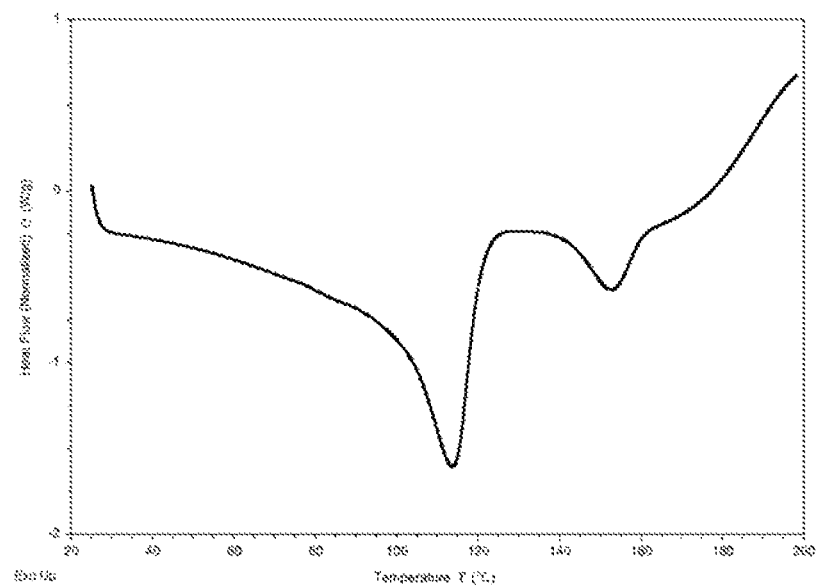
FIG. 3 represents a Differential Scanning Calorimetry (DSC) of Form-C3 of Acalabrutinib

In an embodiment, crystalline Form-C3 of Acalabrutinib is characterized by having a DSC spectrum as shown in FIG. 3.

Figure 4:
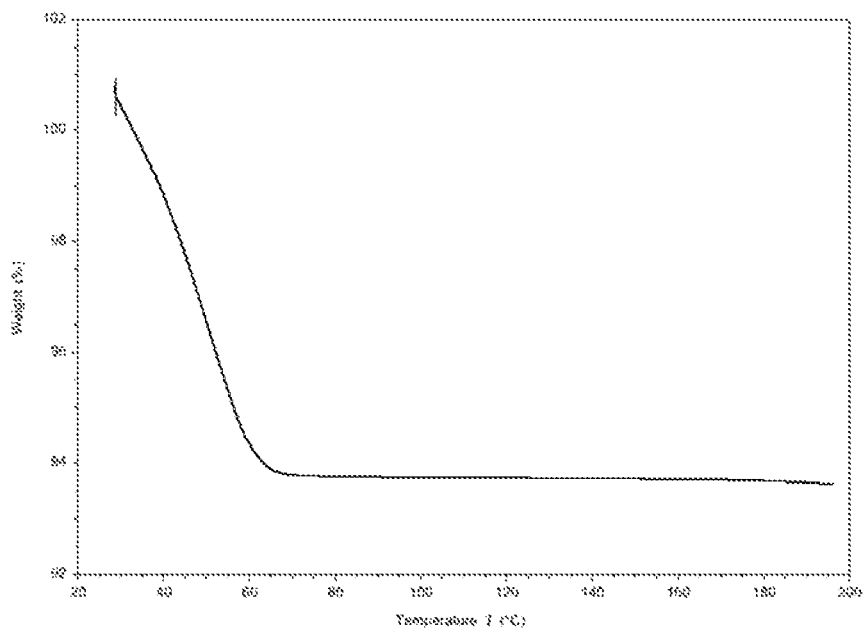
FIG. 4 represents a thermogravimetric analysis (TGA) of Form-C3 of Acalabrutinib

In another embodiment, crystalline Form-C3 of Acalabrutinib is characterized by having a thermogravimetric analysis (TGA) profile as shown in FIG. 4.

In another embodiment, the invention provides process for preparation of crystalline Form-C3 of Acalabrutinib which process involves following steps:
 i) dissolving Acalabrutinib in the suitable solvent at suitable temperature,
 ii) cooling the solution obtained in above step,
 iii) stirring the solution
 iv) filtering the obtained mass.

The suitable solvent used in step i) can be selected from but not limited to acids (such as but not limited to acetic acid, formic acid), esters (such as but not limited to ethyl acetate, isopropyl acetate), ethers (such as but not limited to tetrahydrofuran, 2-methyl tetrahydrofuran, t-butyl methyl ether), alcohols (such as but not limited to methanol, ethanol, isopropanol, t-butanol), ketones (such as but not limited to acetone, methyl isobutyl ketone, methyl ethyl ketone), alkyl nitriles (such as but not limited to acetonitrile, propionitrile), hydrocarbons including halogenated hydrocarbons (such as but not limited to toluene, xylene, dichloromethane), aprotic polar solvents (such as but not limited to sulfolane, dimethyl sulfoxide, N-methyl pyrrolidone), water or mixture thereof.

The suitable temperature used in step i) is preferably higher temperature ranging in between 50° C. to 100° C.

The suitable temperature used in step ii) for cooling may be in the range of −10° C. to 10° C.

The stirring in step iii) is done till precipitation is obtained.

According to third aspect, the present invention provides the crystalline Acalabrutinib which is herein and in the claims designated as "Form-C4", which may be non-hygroscopic (or non-hydroscopic).

In one embodiment, the crystalline Form-C4 is characterized by an X-ray powder diffraction pattern comprising the following 2θ values measured using CuKα, radiation.

In an embodiment, the crystalline Form-C4 has an XRD pattern with characteristics peaks at 8.3, 9.9, 12.1, 15.4, 15.9, 16.7, 19.9, 21.5 and 24.4±0.2° 2θ.

Figure 5:
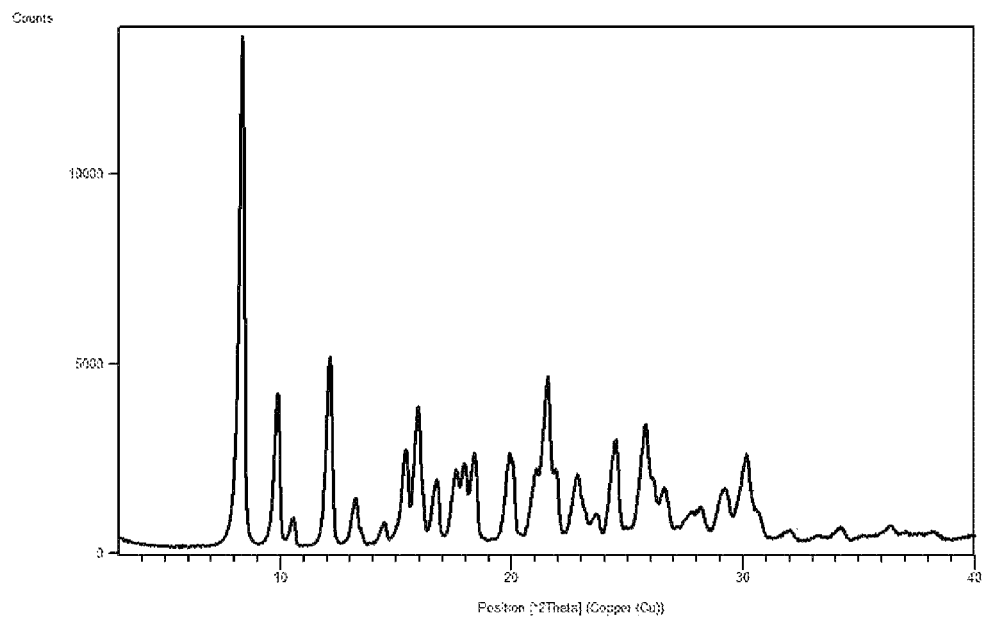
FIG. 5 represents a powder X-ray diffraction pattern of Form-C4 of Acalabrutinib.

Crystalline polymorph C4 of Acalabrutinib may be characterized by powder X-ray diffraction pattern, as shown in FIG. 5.

Crystalline Form-C4 of Acalabrutinib may also be characterized as having a DSC spectrum. The DSC plot for the sample shows one endotherm with an onset at 62.97° C., a peak maximum at 91.72° C.; and a second endotherm with an onset at 146.35° C. and a peak maximum at 157.71° C.

Figure 6:
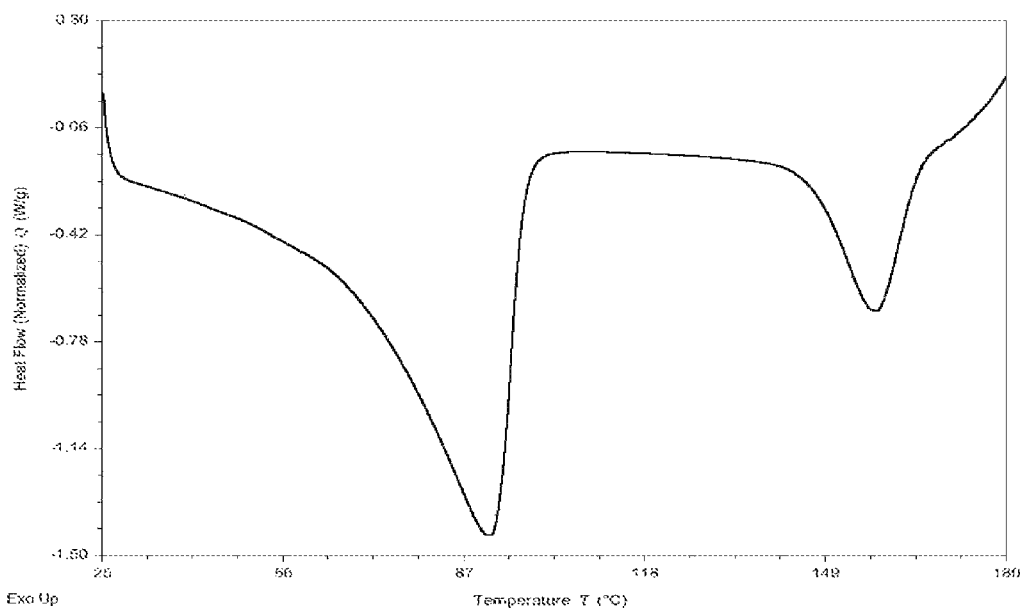
FIG. 6 represents a Differential Scanning Calorimetry (DSC) of Form-C4 of Acalabrutinib

In an embodiment, crystalline Form-C4 of Acalabrutinib is characterized by having a DSC spectrum as shown in FIG. 6.

Crystalline Form-C4 of Acalabrutinib may be a hydrate. In the hydrate of crystalline Form-C4 of Acalabrutinib, water is present in the non-stoichiometric ratio ranging from about 3.0 wt % to about 9.0 wt % per molecule of Acalabrutinib.

Figure 7:
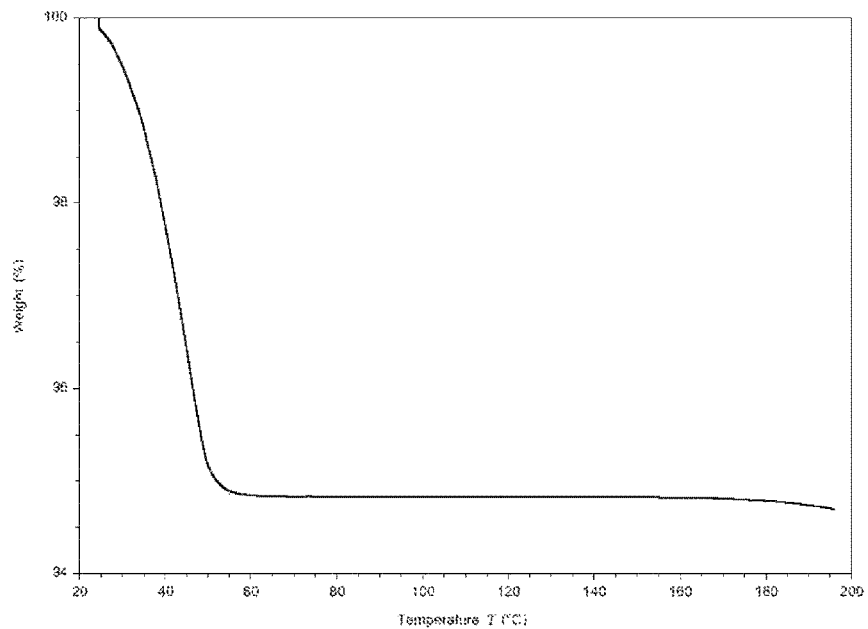
FIG. 7 represents a thermogravimetric analysis (TGA) of Form-C4 of Acalabrutinib

In another embodiment, crystalline Form-C4 of Acalabrutinib is characterized by having a thermogravimetric analysis (TGA) profile as shown in FIG. 7.

Figure 8:
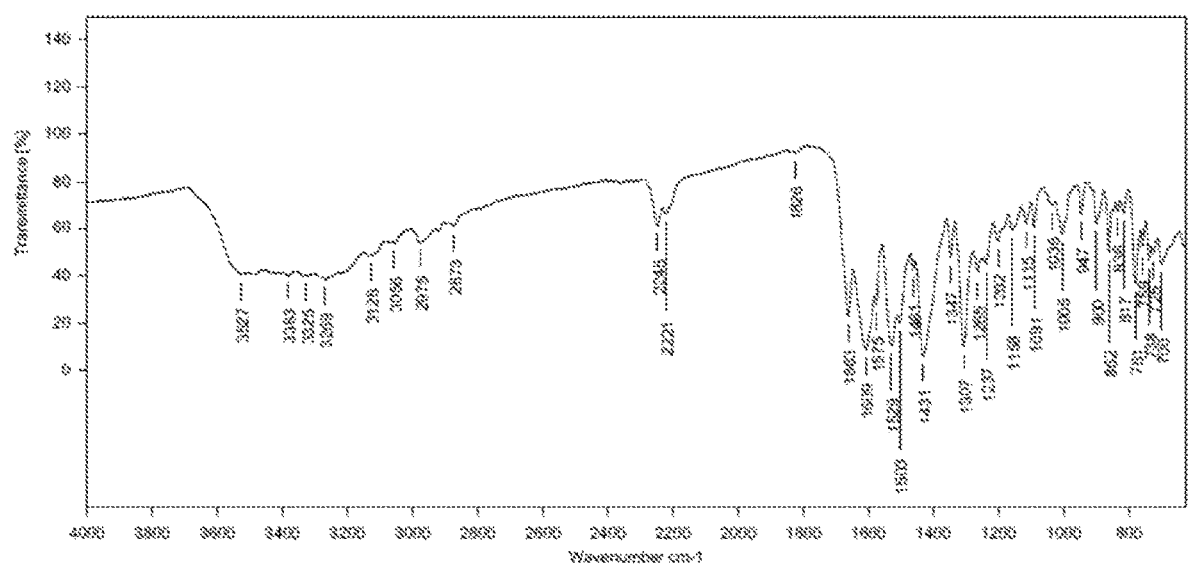
FIG. 8 represents an Infra-Red (IR) absorption spectrum of Form-C4 of Acalabrutinib

In yet another embodiment, crystalline Form-C4 of Acalabrutinib is characterized by having an IR spectrum as shown in FIG. 8.

In another embodiment, the invention provides process for preparation of crystalline Form-C4 of Acalabrutinib which process involves drying the crystalline Form-C3 of Acalabrutinib at a suitable temperature.

The suitable temperature used for drying of Form-C3 may be in the range of 30° to 90° C., preferably 30° to 70° C., more preferably 40° to 60° C. for a period of about 2 hour to about 20 hours, preferably 4 hours to about 15 hours, more preferably for about 6 hours to 12 hours.

According to fourth aspect, the present invention provides the crystalline Acalabrutinib which is herein and in the claims designated as "Form-C5".

In one embodiment, the crystalline Form-C5 is characterized by an X-ray powder diffraction pattern comprising the following 2θ values measured using CuKα, radiation.

In an embodiment, the crystalline Form-C5 has an XRD pattern with characteristics peaks at 7.7, 9.4, 10.8, 13.3, 15.4, 17.3, 22.0 and 23.1±0.2° 2θ.

Figure 9:
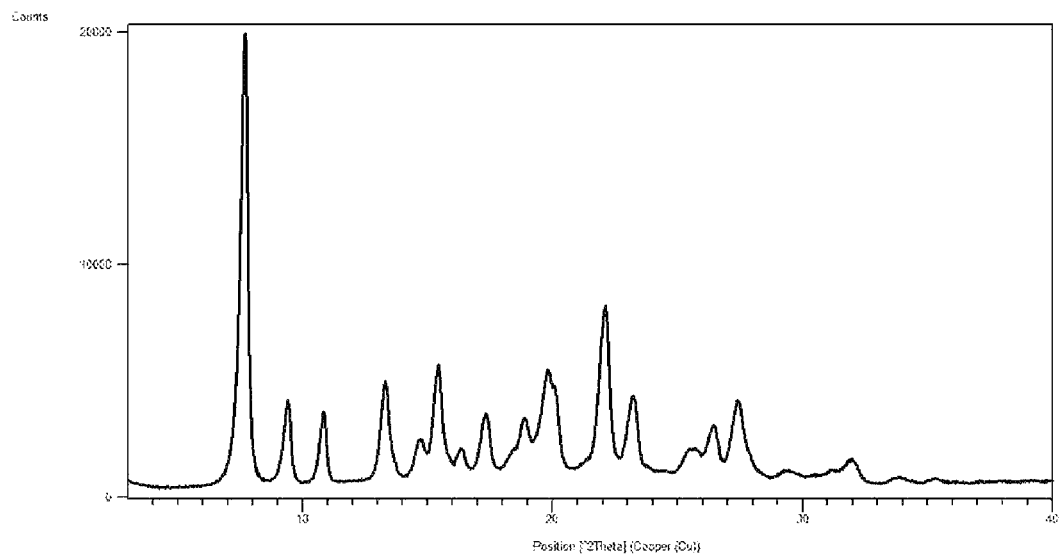
FIG. 9 represents a powder X-ray diffraction pattern of Form-C5 of Acalabrutinib.

Crystalline Form-C5 of Acalabrutinib may be characterized by powder X-ray diffraction pattern, as shown in FIG. 9.

Crystalline Form-C5 of Acalabrutinib may also be characterized as having a DSC spectrum. The DSC plot for the sample shows an endotherm with an onset at 147.70° C., a peak maximum at 158.13° C.

Figure 10:
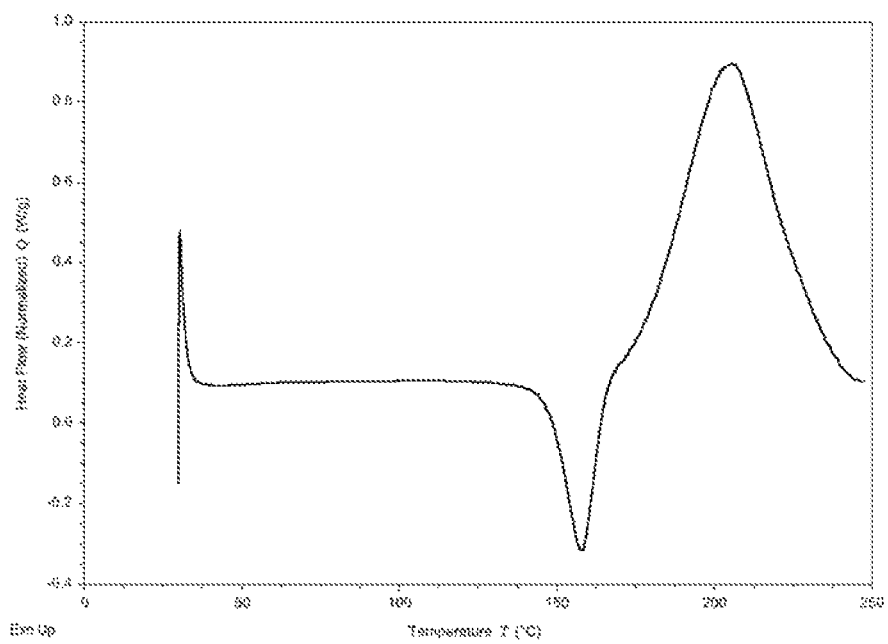
FIG. 10 represents a Differential Scanning Calorimetry (DSC) of Form-C5 of Acalabrutinib

In an embodiment, crystalline Form-C5 of Acalabrutinib is characterized by having a DSC spectrum as shown in FIG. 10.

Figure 11:
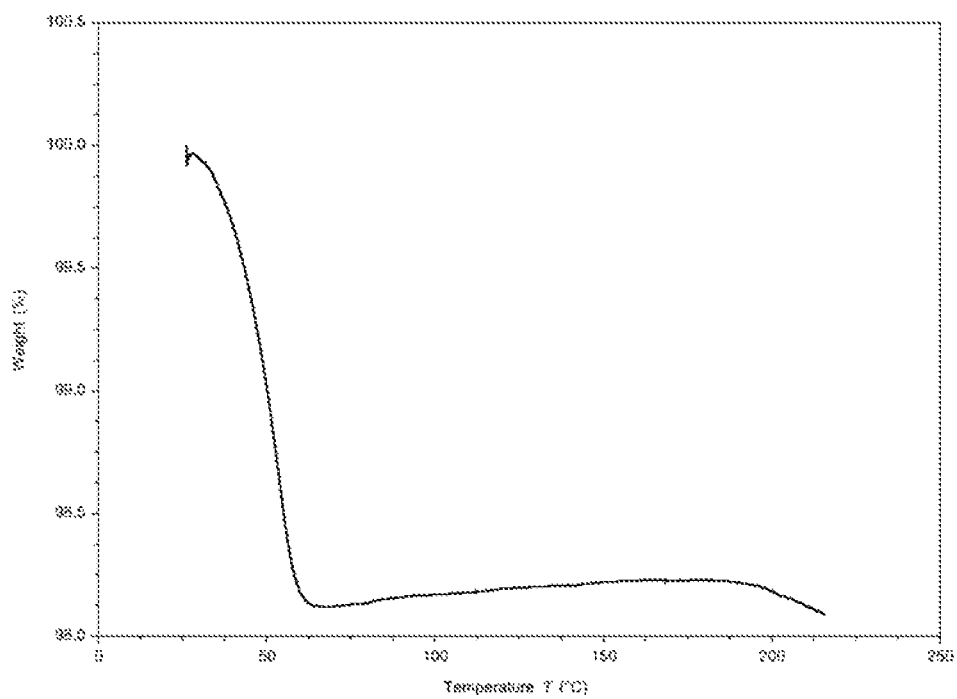
FIG. 11 represents a thermogravimetric analysis (TGA) of Form-C5 of Acalabrutinib

In another embodiment, crystalline Form-C5 of Acalabrutinib is characterized by having a thermogravimetric analysis (TGA) profile as shown in FIG. 11.

In another embodiment, the invention provides process for preparation of crystalline Form-C5 of Acalabrutinib which process involves drying the crystalline polymorph C4 of Acalabrutinib at a suitable temperature.

The suitable temperature used for drying of form C4 may be in the range of 80° to 150° C., preferably 100° to 140° C., more preferably 120° to 130° C. for a period of about 1 hour to about 10 hours, preferably 2 hours to about 8 hours, more preferably for about 3 hours to 5 hours.

Those skilled in the art will recognize that these polymorphic forms may be further characterized by other methods including, but not limited to Infra-red (IR), differential scanning calorimetry (DSC), thermo-gravimetric analysis (TGA), dynamic vapour sorption (DVS), intrinsic dissolution, solid state NMR and Raman spectroscopy. Further bulk and tapped density of the polymorphic forms may also be evaluated.

In one embodiment, the Form-C2, Form-C3, Form-C4 or Form-C5 of Acalabrutinib contain less than 5% by weight total impurities.

In one embodiment, the Form-C2, Form-C3, Form-C4 or Form-C5 of Acalabrutinib is at least 50% pure, or at least 75% pure, or at least 80% pure, or at least 90% pure, or at least 95% pure, or at least 98% pure.

The crystalline Form-C2, Form-C3, Form-C4 or Form-C5 of Acalabrutinib, obtained according to the present invention is substantially free from other forms of Acalabrutinib, "Substantially free" from other forms of Acalabrutinib, shall be understood to mean that the polymorphs of Acalabrutinib, contain less than 10%, preferably less than 5%, of any other forms of Acalabrutinib and less than 1% of other impurities.

The process of the present invention may be used as a method for purifying any form of Acalabrutinib, as well as for the preparation of the new polymorphic forms and salts thereof.

Acalabrutinib, used as a starting material in the present invention for the preparation of crystalline forms C2, C3, C4 and C5 may be prepared by methods known in the art such as those described in WO2013010868.

The present invention comprises 1) a pharmaceutical composition comprising any one, or combination of Acalabrutinib crystalline forms C2, C3, C4 or C5 described above and at least one pharmaceutically acceptable excipient; and 2) the use of any one, or combination, of the above-described Acalabrutinib crystalline forms C2, C3, C4 or C5, in the manufacture of a pharmaceutical composition, wherein the pharmaceutical composition can be useful for the treatment or prevention of mantle cell lymphoma (MCL).

The pharmaceutical composition can be prepared by a process comprising combining any one, or combination of the above-described Acalabrutinib crystalline forms C2, C3, C4 or C5; with at least one pharmaceutically acceptable excipient.

Any one, or combination, of the above-mentioned Acalabrutinib crystalline forms C2, C3, C4 or C5 particularly in a pharmaceutical composition and dosage form, can be used to treat or prevent mantle cell lymphoma (MCL) in a mammal such as a human, comprising administering a treatment effective amount of the one, or combination, of the Acalabrutinib crystalline forms C2, C3, C4 or C5 in the mammal.

Having described the invention with reference to certain preferred embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Example 1

Preparation of Form-C2:

3.0 g of Acalabrutinib was charged in to the 100.0 ml round bottom flask, then 30.0 ml toluene was charged in to the above flask at 20° C. to 25° C. The reaction mass was stirred at high temperature at about 70° C. to 80° C. for 1 to 2 hours. The reaction mass was cooled to 20° C. to 25° C. and the material obtained was filtered using Buchner funnel. The resultant powder was dried at about 70° C. for 2 hours to obtain the desired form.

Example 2

Preparation of Form-C3:

3.0 g Acalabrutinib was dissolved in 10 volumes of Methanol-Water (95:5) solvent mixture at high temperature at about 70° C. to 80° C. The so obtained solution was cooled to −5° C. and stirred for 20 to 30 min. The material obtained was filtered under vacuum to obtain the title compound.

Example 3

Process to Prepare Form-C4:

The crystalline Form-C3 was dried in a vacuum try drier at 50° C. for 3 to 4 hours to obtain the desired compound.
Purity: 99.68%
Total impurities: <1%

Example 4

Process to Prepare Form-C5:

The crystalline Form-C4 was dried in vacuum try drier at 120° C. for 3 to 4 hours to obtain the desired compound.

We claim:

1. A crystalline form of acalabrutinib, selected from:
   crystalline form-C3 characterized by X-ray powder diffraction (XRPD) pattern peaks at 8.5, 10.0, 11.7, 12.9, 15.3, 17.9, 18.3, 20.1 and 21.6±0.2° 2Θ;
   crystalline form-C4 characterized by X-ray powder diffraction (XRPD) pattern peaks at 8.3, 9.9, 12.1, 15.4, 15.9, 16.7, 19.9, 21.5, and 24.4±0.2° 2Θ; and
   crystalline form-C5 characterized by X-ray powder diffraction (XRPD) pattern peaks at 7.7, 9.4, 10.8, 13.3, 15.4, 17.3, 22.0, and 23.1±0.2° 2Θ.

2. The crystalline form-C4 of claim 1, wherein the crystalline form is characterized by a DSC substantially as depicted in FIG. 6.

3. The crystalline form of claim 1, wherein the crystalline form C4 contains less than 5% by weight total impurities.

4. The crystalline form of claim 1, wherein the crystalline form C4 is at least 50% pure.

5. A pharmaceutical composition comprising one or more of a Form-C3, Form-C4 or Form-C5 of acalabrutinib and a pharmaceutically acceptable carrier.

6. The pharmaceutical composition of claim 5, further comprising one or more pharmaceutically acceptable excipients.

* * * * *